US00PP19568P2

(12) United States Plant Patent
Ikeda et al.

(10) Patent No.: US PP19,568 P2
(45) Date of Patent: Dec. 9, 2008

(54) ***FUCHSIA* PLANT NAMED 'SANIFPIRAVE'**

(50) Latin Name: *Fuchsia×hybrida*
Varietal Denomination: Sanifpirave

(75) Inventors: Mito Ikeda, Hyogo (JP); Yasuo Kishimoto, Hyogo (JP); Hidefumi Funakoshi, Hyogo (JP); Yasuyuki Murakami, Shiga (JP)

(73) Assignees: Suntory Flowers Limited, Tokyo (JP); Nishinomiya City, Hyogo (JP)

( * ) Notice: Subject to any disclaimer, the term of this patent is extended or adjusted under 35 U.S.C. 154(b) by 0 days.

(21) Appl. No.: 11/998,803

(22) Filed: Nov. 30, 2007

(51) Int. Cl.
*A01H 5/00* (2006.01)

(52) U.S. Cl. ..... Plt./300

(58) Field of Classification Search ..... Plt./300
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Fuchsia* plant named 'Sanifpirave', characterized by its compact and outwardly arching growth habit; freely branching plant habit; lavender and light purple bi-colored flowers; freely and continuous flowering habit; long flowering period; and tolerance to low and high temperatures.

1 Drawing Sheet

Botanical designation: *Fuchsia×hybrida.*
Cultivar denomination: 'Sanifpirave'.

BACKGROUND OF THE INVENTION

The present invention relates to a new and distinct cultivar of *Fuchsia,* botanically known as *Fuchsia×hybrida* and hereinafter referred to by the name 'Sanifpirave'.

The new *Fuchsia* is a product of a planned breeding program conducted by the Inventors in Nishinomiya, Hyogo, Japan. The objective of the breeding program is to create new outwardly arching *Fuchsia* cultivars with numerous flowers and attractive flower coloration.

The new *Fuchsia* originated from a cross-pollination made by the Inventors in 2003 in Nishinomiya, Hyogo, Japan of a proprietary selection of *Fuchsia×hybrida* identified as code number ajf-52, not patented, as the female, or seed, parent with a proprietary selection of *Fuchsia×hybrida* identified as code number ard-2, not patented, as the male, or pollen, parent. The new *Fuchsia* was discovered and selected by the Inventor as a single flowering plant within the progeny of the stated cross-pollination in a controlled environment in Nishinomiya, Hyogo, Japan.

Asexual reproduction of the new Fuchsia by terminal cuttings in a controlled environment in Nishinomiya, Hyogo, Japan and Higashiomi, Shiga, Japan since January, 2004, has shown that the unique features of this new Fuchsia are stable and reproduced true to type in successive generations.

SUMMARY OF THE INVENTION

The cultivar Sanifpirave has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sanifpirave'. These characteristics in combination distinguish 'Sanifpirave' as a new and distinct cultivar of *Fuchsia:*

1. Compact and outwardly arching growth habit.
2. Freely branching plant habit; bushy habit.
3. Lavender and light purple bi-colored flowers.
4. Freely and continuous flowering habit; long flowering period.
5. Tolerant to low and high temperatures.

Plants of the new *Fuchsia* differ primarily from plants of the female parent selection in the following characteristics:

1. Plants of the new *Fuchsia* have smaller leaves than plants of the female parent selection.
2. Plants of the new *Fuchsia* have smaller flowers than plants of the female parent selection.
3. Plants of the new *Fuchsia* and the female parent selection differ in sepal shape.

Plants of the new *Fuchsia* differ primarily from plants of the male parent selection in the following characteristics:

1. Plants of the new Petunia are more outwardly spreading than and are not as upright as plants of the male parent selection.
2. Plants of the new *Fuchsia* have darker green-colored leaves than plants of the male parent selection.
3. Plants of the new *Fuchsia* and the male parent selection differ in flower coloration and form.

Plants of the new *Fuchsia* can also be compared to plants of the cultivar Sanihanf arl2, disclosed in U.S. Plant Pat. No. 16,779. In side-by-side comparisons conducted in Nishinomiya, Hyogo, Japan, plants of the new *Fuchsia* and the cultivar Sanihanf arl2 differed in the following characteristics:

1. Plants of the new *Fuchsia* were not as cascading as plants of the cultivar Sanihanf arl2.
2. Plants of the new *Fuchsia* had longer internodes than plants of the cultivar Sanihanf arl2.
3. Plants of the new *Fuchsia* had smaller leaves than plants of the cultivar Sanihanf arl2.
4. Plants of the new *Fuchsia* had larger flowers than plants of the cultivar Sanihanf arl2.

5. Plants of the new *Fuchsia* and the cultivar Sanihanf arl2 differed in flower color as plants of the cultivar Sanihanf arl2 had red purple and white bi-colored flowers.
6. Plants of the new *Fuchsia* had broader sepals than plants of the cultivar Sanihanf arl2.
7. Plants of the new *Fuchsia* had shorter peduncles than plants of the cultivar Sanihanf arl2.

BRIEF DESCRIPTION OF THE PHOTOGRAPHS

The accompanying colored photographs illustrate the overall appearance of the new *Fuchsia,* showing the colors as true as it is reasonably possible to obtain in colored reproductions of this type. Colors in the photographs may differ slightly from the color values cited in the detailed botanical description which accurately describe the colors of the new *Fuchsia.*

The photograph at the top of the sheet comprises a side perspective view of a typical flowering plant of 'Sanifpirave' grown in a container.

The photograph at the bottom of the sheet is a close-up of typical flowers of 'Sanifpirave'.

DETAILED BOTANICAL DESCRIPTION

The aforementioned photographs and following observations, measurements and values describe plants grown in Nishinomiya, Hyogo, Japan, under commercial practice in a polyethylene-covered greenhouse with day temperatures ranging from 15° C. to 32° C. and night temperatures ranging from 10° C. to 25° C. Plants were grown for about one year with one plant per 13.5-cm container. In the following description, color references are made to The Royal Horticultural Society Colour Chart, 2001 Edition, except where general terms of ordinary dictionary significance are used.

BOTANICAL CLASSIFICATION:

*Fuchsia×hybrida* cultivar Sanifpirave.

Parentage:

*Female, or seed, parent.*—Proprietary selection of *Fuchsia×hybrida* identified as code number ajf-52, not patented.

*Male, or pollen, parent.*—Proprietary selection of *Fuchsia×hybrida* identified as code number ard-2, not patented.

Propagation:

*Type.*—By terminal cuttings.

*Time to initiate roots.*—About one week at temperatures of 20° C.

*Time to produce a rooted young plant.*—About three weeks at temperatures of 20° C.

*Root description.*—Fine, fibrous; yellowish white in color.

*Rooting habit.*—Freely branching.

Plant description:

*Plant and growth habit.*—Initially upright, then outwardly spreading; compact. Freely branching; with lateral branches developing potentially at every node; bushy habit. Vigorous growth habit.

*Plant height.*—About 25 cm.

*Plant diameter.*—About 35 cm.

Lateral branch description:

*Length.*—About 20 cm.

*Diameter.*—About 2.6 mm.

*Internode length.*—About 2.8 cm.

*Strength.*—Strong.

*Aspect.*—Initially upright to outwardly arching.

*Texture.*—Pubescent.

*Color.*—Close to N79B.

Foliage description:

*Arrangement.*—Opposite, simple.

*Length.*—About 4.6 cm.

*Width.*—About 2.5 cm.

*Shape.*—Ovate.

*Apex.*—Acute.

*Base.*—Obtuse.

*Margin.*—Dentate.

*Texture, upper and lower surfaces.*—Sparsely pubescent.

*Venation pattern.*—Pinnate; reticulate.

Color. —Developing foliage, upper surface: Close to 143A. Developing foliage, lower surface: Close to 143B. Fully expanded foliage, upper surface: Close to 137A; venation, close to 137A. Fully expanded foliage, lower surface: Close to 147B; venation, close to 147B.

*Petiole.*—Length: About 5.7 mm. Diameter: About 1.2 mm. Texture, upper and lower surfaces: Smooth, glabrous. Color, upper and lower surfaces: Close to 60A.

Flower description:

*Flower arrangement and habit.*—Single bi-colored axillary flowers. Flowers pendulous. Flowers not fragrant. Freely flowering habit with potentially two flowers per leaf axil.

*Natural flowering season.*—Long flowering period; in Japan, plants flower from spring to autumn; flowering continuous during this period. Flowers last about three to four days on the plant. Flowers not persistent.

*Flower diameter.*—About 5 cm.

*Flower height* (*depth*).—About 3.5 cm.

*Flower buds.*—Shape: Globose. Length: About 2.8 cm. Diameter: About 1.6 cm. Color: Close to 65A.

*Petals.*—Arrangement: Typically four, occasionally five or six, in a single whorl. Length: About 2.5 cm. Width: About 2.4 cm. Shape: Obovate. Apex: Truncate. Base: Obtuse. Margin: Entire. Texture, upper and lower surfaces: Smooth, glabrous; satiny. Color: When opening, upper and lower surfaces: Close to 85A. Fully opened, upper and lower surfaces: Close to 84B.

*Sepals.*—Arrangement: Calyx star-shaped with four sepals fused at the base. Length: About 2.9 cm. Width: About 1.3 cm. Shape: Oblong. Apex: Acute. Margin: Entire. Texture, upper and lower surfaces: Smooth, glabrous; satiny. Color: When opening and fully opened, upper surface: Close to 55C; towards the apex, 157D. When opening and fully opened, lower surface: Close to N57D.

*Peduncles.*—Length: About 3.1 cm. Diameter: About 1.1 mm. Angle: Arching. Strength: Moderately strong. Texture: Sparsely pubescent. Color: Close to 143C.

*Reproductive organs.*—Stamens: Quantity: Eight per flower. Anther shape: Ellipsoidal. Anther size: About 3.8 mm by 2 mm. Anther color: Close to 51C. Pollen amount: Moderate. Pollen color: Close to 2D. Pistils: Quantity: One per flower. Pistil length: About 5.8 cm. Style color: Close to 55C. Stigma shape: Conical. Stigma color: Close to 23D. Ovary color: Close to 144A.

*Seed/fruit.*—Seed and fruit development have not been observed on plants of the new *Fuchsia*.

Temperature tolerance: Plants of the new *Fuchsia* have good temperature tolerance and have been observed to tolerate temperatures ranging from about −2° C. to about 33° C.

Pathogen/pest resistance: Plants of the new *Fuchsia* have not been observed to be resistant to pests and pathogens common to *Fuchsia*.

It is claimed:

1. A new and distinct *Fuchsia* plant named 'Sanifpirave' as illustrated and described.

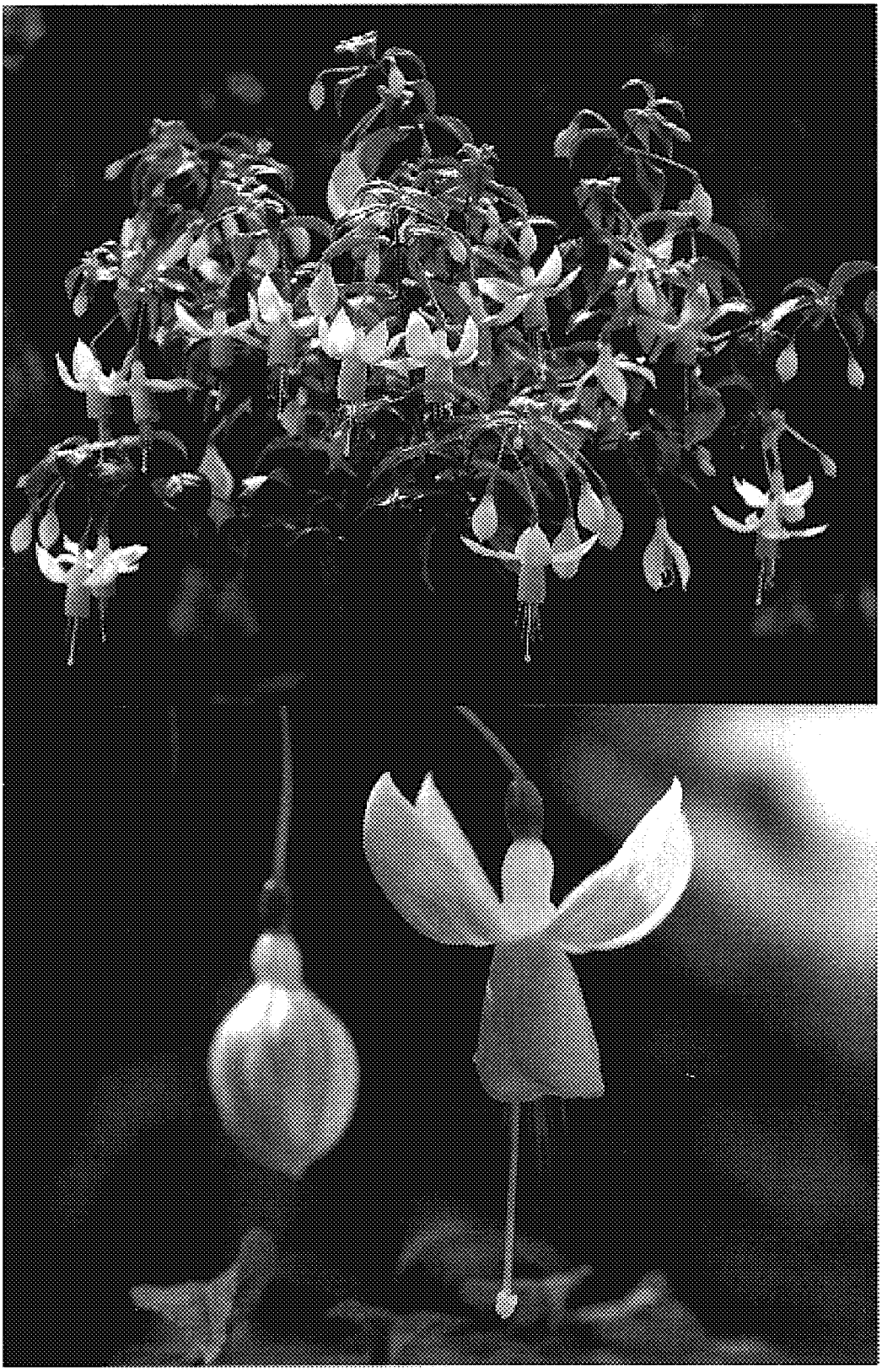

* * * * *